(12) United States Patent
Klokkers et al.

(10) Patent No.: US 6,248,758 B1
(45) Date of Patent: Jun. 19, 2001

(54) PHARMACEUTICAL ANTACID

(75) Inventors: Karin Klokkers; Marion Kutschera; Wilfried Fischer, all of Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/319,895

(22) PCT Filed: Mar. 13, 1998

(86) PCT No.: PCT/EP98/01478

§ 371 Date: Sep. 8, 1999

§ 102(e) Date: Sep. 8, 1999

(87) PCT Pub. No.: WO98/40069

PCT Pub. Date: Sep. 17, 1998

(30) Foreign Application Priority Data

Mar. 13, 1997 (EP) .................................................. 97104200

(51) Int. Cl.[7] ................ A61K 31/4439; A61K 31/4184; A61K 9/16; A61K 9/20
(52) U.S. Cl. ........................ 514/338; 546/273.7; 424/475
(58) Field of Search ............................ 514/338; 424/475; 546/273.7

(56) References Cited

U.S. PATENT DOCUMENTS

| | | | |
|---|---|---|---|
| 5,219,870 | * 6/1993 | Kim, I .................................. | 514/338 |
| 5,232,706 | * 8/1993 | Coll ...................................... | 424/475 |
| 5,399,700 | * 3/1995 | Min, I et al. ........................ | 546/271 |
| 5,817,338 | * 10/1998 | Bergstrand et al. ................. | 424/468 |
| 5,879,708 | * 3/1999 | Making et al. ...................... | 424/475 |

FOREIGN PATENT DOCUMENTS

| | | | |
|---|---|---|---|
| 3427786 | * 1/1986 | (DE) . | |
| 3427787 | * 1/1986 | (DE) . | |
| 0444625 | * 9/1991 | (EP) . | |
| 93-13138 | * 7/1993 | (WO) . | |
| 94-02140 | * 2/1994 | (WO) . | |
| 96-24338 | * 8/1996 | (WO) . | |
| 96-38175 | * 12/1996 | (WO) . | |

OTHER PUBLICATIONS

Hwang Et Al., Chemical Abstracts, vol. 124, 211738, Apr. 1996.*

Ooishi Et Al., Chemical Abstracts, vol. 119, 234039, Nov. 1993.*

Kim III, WPI Derwent, 93–255964 132, 1993.*

* cited by examiner

Primary Examiner—Floyd D. Higel
(74) Attorney, Agent, or Firm—Pitney, Hardin, Kipp & Szuch, LLP

(57) ABSTRACT

A pharmaceutical formulation comprising a benzimidazole derivative as active ingredient, and as excipients, at least one cyclodextrin and at least one amino acid.

28 Claims, No Drawings

PHARMACEUTICAL ANTACID

This application is a 371 of PCT/EP98/01478 filed March 3, 1998.

The present invention relates to stable pharmaceutical formulations, containing moisture and acid sensitive benzimidazole derivatives (e. g. omeprazole) as pharmaceutically active ingredient combined with amino acids and cyclodextrins as excipients, and to a method for preparation such pharmaceutical formulations.

Omeprazole (5-methoxy-2-2(4-methoxy-3,5-dimethyl-2-pyridinyl-methyl-sulfinyl)-1H-benzimidazol) is an effective inhibitor of gastric acid secretion and has a strong antiulcer activity. It is known, that omeprazole rapidly decomposes at acidic and neutral pH. Furthermore moisture, organic solvents and UV-irradiation accelerate the degradation of omeprazole too, causing discoloration of the substance in solution, as well as in solid form. For example, omeprazole has half-life time of 10 minutes in an aqueous solution of below a pH-value of 4, but 18 hours at pH 6,8 and about 300 days at pH 11 (M. Mathew and co-workers, Drug. Dev. Ind. Pharm., 21,965,1995). The drug has been reported to be stable under alkaline conditions [Pilbrant A° and Cederberg C. Scand. J. Gastroenterology, Suppl. 108, 113–120(1985)]. According to A. Brändström and co-workers (Acta Chem. Scand. 43,536,1989) the acid-catalyzed degradation kinetics of omeprazole is very complicated, the primary degradation is followed by rather complex secondary reactions.

Several methods for stabilizing the acid-unstable compound, in particular omeprazole have been described.

Some patent applications (U.S. Pat. No. 5,232,706, EPA-0567201 A2, EPA-0519144 A1, EPA-0496437 A2, U.S. Pat. No. 5,385,739, DEA-1204363 and EPA-0247983 B1) claim a common method to overcome this stability problem by applying an inert protective layer between the core and the enteric coating layer. The core contains the pharmaceutical active substance (omeprazole) or its salts, alkaline or acid neutralizing additives, alkaline salts or a combination thereof.

The resorption of omeprazole occurs in the upper duodenum. Therefore, a quick and complete release of the active ingredient after passage of the pylorus must be ensured in order to guarantee a sufficiently high bioavailability. For this, omeprazole is provided with a coating of enteric, i.e. gastric juice-resistant material, which is insoluble in the acid environment of the stomach (ca. pH 1 to 3) on the one hand, but dissolves in the weakly acidic to weakly alkaline region of the duodenum (pH>5,5). ordinary enteric coatings, however, are made of acidic compounds. If the core containing omeprazole will be covered with a conventional enteric coating without an subcoating, omeprazole rapidly decomposes by direct or indirect contact with the coating, with the result that the preparation become discolored.

Although the sensitivity of omeprazole against organic solvent is known, acetone and methylene-chloride (EPA-0496437 A2, EPA-0567201 A2) or acetone and ethanol (USP-5385739, EPA-0519144 A1) are used for the enteric coating of the tablets. This treatment can damage the active ingredient during the enteric coating process or during the long-term storage.

All known procedures consist of complicated multi-step operations and result in expensive final products, which must be stored under specific conditions in moisture proof packages.

DE-427785 A1, DE-3427786 A1, DE-3427787 A1 intended to solve the stability problems of omeprazole by a different method. Omeprazole and β-cyclodextrin (CD) or derivatives of β-CD (hydroxypropylcyclodextrin) were reacted in 96% ethanol for 15 hours at elevated temperature. Upon cooling a white crystalline substance was isolated, which was believed to be an omeprazole/β-CD inclusion complex. However the elevated temperature through 15 hours in the presence of 96% ethanol results in ex-tensive degradation of omeprazole thus there is hardly active ingredient remained in the isolated product. It is generally known, that ethanol is a competing cyclodextrin-complex forming agent. From a 96% ethanolic system only the crystalline etha-nol/β-CD complex can be isolated by using the mentioned method (Otagiri, M. et al: Acta Pharm. Suetica 21, 357 (1984), Pitha, J. and Hoshino, T.: Int. J. Pharm 80, 234 (1992)).

The WO 93/13138 discloses a method for stabilization of acid-sensitive benzimidazoles, more specifically for the stabilization of omeprazole in drug formulations, which comprise a cyclodextrin-complex of omeprazole, a protective inert layer and an enteric coating. The omeprazole is reacted in presence of alkaline hydroxides, alkaline salts, amines or buffers with cyclodextrin and derivatives for 1 to 30 minutes at 30 to 70° C. in a homogeneous solution system. After cooling to room temperature the reacted solution is allowed to stand at 4° C. for 3 to 15 hours to form the omeprazole/cyclodextrin-complex. The isolated inclusion-complex is washed with some cooled water several times to completely remove the remaining alkaline component on the inclusion complex. Alternatively, from the reacted solution the water might be removed by spray drying, freeze drying or vacuum evaporating for isolation of the inclusion complex powder as stable compound.

In the state of the art a core made of omeprazole and an alkaline substance as well as a inclusion complex from omeprazole and cyclodextrin without an amino acid is not stable enough. A inert protective layer is necessary to guarantee the stability of omeprazole and specific moisture-proof packages were needed for storing the final product.

Main object of the invention is to guarantee a stabilization of benzimidazoles such as omeprazole as active ingredient by forming a benzimidazole/cyclodextrin inclusion complex.

It has now been found, that benzimidazoles such as omeprazole can be stabilized by complexation with a cyclodextrin such as β-cyclodextrin in the presence of an amino acid. It has further been found that in this case surprisingly no additional inert or enteric layer is needed to protect particles or a core containing the benzimidazole/cyclodextrin complex and an amino acid. Merely optionally the core may be coated directly with an enteric coating layer.

Thus, the problem underlying the invention is solved by a pharmaceutical formulation comprising or consisting of
  a benzimidazole derivative as active ingredient, and as excipients
  at least one cyclodextrin and
  at least one amino acid.

The present invention does provide a new pharmaceutical benzimidazole formulation with improved stability features and simplified preparation process.

The benzimidazole derivative can be a compound which is decomposed in the presence of humidity and especially at a pH'11, especially '7. Examples for these benzimidazole derivatives are omeprazole, lansoprazole, leminoprazole, rabeprazole, and pantoprazole. Omeprazole is preferred.

Further, a specific embodiment of the invention concerns a pharmaceutical formulation, wherein the inclusion complex forming agent is β-cyclodextrin, mono- or polyalkylated β-cyclodextrin, mono- or polyhydroxyalkylated β-cyclodextrin or γ-cyclodextrin, preferably β-cyclodextrin.

The amino acid useful for the pharmaceutical formulation according to the invention can be an alkaline amino acid, preferably arginine, lysine or hydroxy lysine and especially L-arginine, L-lysine or L-hydroxy lysine; an alkaline dipeptide or a pharmaceutically acceptable alkaline amino acid derivate.

Further, a specific embodiment of the invention concerns a pharmaceutical formulation, wherein the molar ratio of omeprazole to cyclodextrin is 1 to 10 and preferably 1 to 2.

Further, a specific embodiment of the invention concerns a pharmaceutical formulation, wherein the molar ratio of the amino acid (preferably L-arginine) to omeprazole is 0.5 to 10 and preferably 1 to 1.

Further, a specific embodiment of the invention concerns a pharmaceutical formulation, wherein the formulation is a powdered, pelletized or granulated form, optionally processed to tablets.

The pharmaceutical formulation according to the invention can be characterized in that the particles of the powder, of the granulate or of the pelletized formulation are not coated with an enteric coating. The powder, the granulate or the pelletized formulation can be, however, contained in capsules which can optionally be provided with an enteric coating.

Further, the particles of the powder, of the granulate or of the pelletized formulation can be provided with an enteric coating and optionally be contained in capsules which are not provided with an enteric coating.

As examples for enteric coating materials polymeres such as cellulose acetate phthalate, hydroxypropyl methylcellulose phthalate, copolymerized methacrylic acid/methacrylic acid methyl esters or water-based polymer dispersions, for instance, compounds known under the trade name Eudragit® L (Röhm Phar-ma), or similar compounds can be used. The enteric coating layer can optionally contain a pharmaceutically acceptable plasticizer such as dibutylphthalate, diethylsebacat or tri-ethylcitrat. Dispersants such as talc, colorants and pigments may also be included to the enteric coating layer.

The problem underlying the invention is, in addition, solved by a process for the production of a pharmaceutical composition according to the invention, wherein
 (i) a benzimidazole derivative, at least one cyclodextrin, and at least one amino acid are wetted with water and mixed;
 (ii) the resulting mixture is dried.

Further, the problem underlying the invention is solved by a process for the production of a pharmaceutical composition according to the invention, wherein
 (i) a benzimidazole derivative, at least one cyclodextrin, and at least one amino acid are wetted with water and mixed;
 (ii) the resulting mixture is dried; and
 (iii) discoloration of the composition is examined and if a discolored product is obtained, said discolored product is discarded, another amino acid is selected and steps (i) to (iii) are repeated until an uncolored product is obtained.

The mixing in step (i) of the process according to the invention can be carried out by wet-kneading.

The water to be used in step (i) of the process according to the invention can be ammoniacal water or can be free of any ammonia.

The drying in step (ii) of the process according to the invention can be carried out by freeze-drying, spray-drying or vacuum-drying.

For the production of pellets the pharmaceutical formulation according to the invention can be mixed with a binding agent such as microcrystalline cellulose and an excipient such as hydroxypropylcellulose and moistened, for example with isopropanol, and then formulated into pellets by conventional pharmaceutical procedures. The pellets can be used as cores for further processing. The pellets may be filled directly into capsules which are optionally coated with an enteric coating. Further, the pellets themselves may be coated with an enteric coating and optionally filled into uncoated capsules.

The enteric coating layer can be applied onto the pellets by conventional coating techniques such as, for instance, pan coating, fluidized bed coating, fluidized bed bottom sprayed coating or a Turbo Jet-Technology for the production of large amounts using dispersions of polymers in water and/or suitable organic solvents or by using latex suspensions of said polymers Examples for enteric coating polymers have already been mentioned.

An application of the pharmaceutical formulation according to the invention results in pharmaceutically effective plasma levels and offers a sufficiently high bioavailability. This could not be expected in view of the fact that the active ingredient is used in combination with a complexing agent.

In order to describe the invention more specifically but without intending to limit the scope of the invention in any way the following examples are presented:

EXAMPLE 1 AND COMPARATIVE EXAMPLES

Compositions containing omeprazole, β-cyclodextrin and an amino acid at a molar ratio of 1:2:1 were prepared by kneading in presence of water and powdered after drying. Cellulose acetate phthalate, an acidic reacting excipient, was mixed to the composition in an amount of 5w/w %, calculated to the total weight of the sample. The optical density of the composition powders after storing for 7 days at 60° C. in presence of 96% R.H. is illustrated in Table I.

TABLE I

Composition and discoloration (optical density measured at 346 nm) of omeprazole + β-cyclodextrin mixtures, in presence of amino acids and cellulose acetate phthalate after 7 days at 60° C. and 96% relative humidity

| Sample | omeprazole | β-CD | amino acid | cellulose acetate phthalate | O.D. after dissolving the powders |
|---|---|---|---|---|---|
| A | + | + |  |  | 1.0 |
| B | + | + |  | + | 2.4 |
| C | + | + | arginine |  | 0.4 |
| D | + | + | arginine | + | 0.8 |
| E | + | + | lysine |  | 0.6 |
| F | + | + | lysine | + | 0.7 |

The presence of an amino acid enhances the stability of the inclusion complex of omeprazole and β-cyclodextrin as illustrated in Table I. There is no rapid decomposition of omeprazole by direct contact with cellulose acetate phthalate under stressed conditions.

COMPARATIVE EXAMPLE

Inclusion complexes of omeprazole and β-cyclodextrin were prepared by the same method as described before but without using an amino acid.

As reference omeprazole and lactose mixtures were prepared, with similar weight-ratios. The molar ratio of omeprazole to β-cyclodextrin and to lactose was 1:2. The result is illustrated in Table II.

TABLE II

Composition and discoloration of powder mixtures stored at 40° C. at 76% R.H. for 20 days

| samples | omeprazole | β-CD | lactose | cellulose acetate phthalate | stored in closed container | stored in open container | O.D. after dissolving the powders |
|---|---|---|---|---|---|---|---|
| G | + |   | + |   | + |   | 0,2 |
| H | + |   | + | + | + |   | 0,4 |
| J | + | + |   |   | + |   | 0,2 |
| J | + | + |   | + | + |   | 0,4 |
| K | + |   | + |   |   | + | 0,8 |
| L | + |   | + | + |   | + | 2,4 |
| M | + | + |   |   |   | + | 0,7 |
| N | + | + |   | + |   | + | 2,0 |

Stability of the inclusion complex in absence of an amino acid seems to be acceptable only by storage in closed containers even in the absence of cellulose acetate phthalate. The pre-sence of cellulose acetate phthalate in all cases enhances the degradation of omeprazole. Comparing the samples stored in closed and in open containers the role of the humidity is quite obvious: the discoloration of omeprazole in open containers is much higher in all cases than in the closed containers. The degradation is significantly accelerated by humidity (samples stored in open containers) and by the presence of cellulose acetate phthalate (acidic additive), the β-cyclodextrin itself is not a significantly better stabilizer than the lactose.

EXAMPLE 2

In further experiments the β-cyclodextrin has been suspended in diluted aqueous ammonium hydroxide solution, before omeprazole and arginine has been added. The samples were prepared as described before and stored at 50° C. and 76% R. H. for 7 days. Cellulose acetate phthalate (CAP) (5% w/w) was mixed to all samples after the β-cyclodextrin/omeprazole/arginine amino acid suspensions were dried and powdered. The composition of the samples as well as their discoloration are shown in Table III.

TABLE III

Excipients added to omeprazole and cellulose acetate phthalate, method of preparation and the discoloration of the samples after storing for 7 days at 50° C. and 76% R.H. in open containers

| Sample | Components | | | Methods of preparation | O.D. of the solution |
|---|---|---|---|---|---|
| O | lactose |   | CAP | powder mixture | 2.4 |
| P | β-CD |   | CAP | powder mixture | 1.6 |
| Q | β-CD + NH₃ |   | CAP | powder mixture | 0.6 |
| R | β-CD | arginine | CAP | powder mixture | 0.8 |
| S | β-CD | arginine | CAP | wet kneading | 0.3 |
| T | β-CD + NH₃ | arginine | CAP | wet kneading | 0.1 |
| U | lactose | arginine | CAP | wet kneading | 1.2 |
| V | β-CD + NH₃ |   | CAP | wet kneading | 0.9 |

These data compared to the data of Table I. and II. clearly demonstrate, that while β-cyclodextrin—when used in wet kneading or in solution—alone is more effective than lactose in protecting omeprazole against discoloration particularly when it is reacted with omeprazole in ammonia-alkaline solution, its protecting effect is significantly potentiated by the presence of arginine or lysine.

The lactose/arginine combination (U) or the β-cyclodextrin+NH₃ without arginine (V) did not result in satisfactory stabilizing effect. The required omeprazole protecting effect (against acid and water provoked decomposition) could be attained by the ternary combination of omeprazole/β-CD/arginine (S-T), prepared by wet kneading in water, wherein the water can be ammonia-alkaline water or water free of ammonia.

During the drying process the ammonia has been completely removed, in the end-product ammonia can not be detected.

Particularly important is that this combination is not sensitive to 76% R. H., at elevated temperature.

EXAMPLE 3

208 g L-arginine are dissolved in 2L distilled water, and 400 g omeprazole are suspended in this solution (Suspension I).

3 kg β-cyclodextrin (water content 11.95%) are suspended with 3.2 L distilled water by Ultra-Turrax for 5 minutes (Suspension II.)

Suspension I is poured into Suspension II. under vigorous stirring by Ultra-Turrax for 15 minutes at 8000 rpm.

For isolation of the solid product the suspension is frozen and the water content is removed by freeze-drying.

Yield: 3242 g (97.3%)

omeprazole content: 12.3%

Water content: 2.5%

Determination of omeprazole content of samples

As it is shown in Table IV., the samples showed a good storage stability. The decrease of the omeprazole content in the samples—stored under stressed conditions—does not exceed an absolute value of 0.5%, at samples—stored at ambient temperature— practically no change in active ingredient content was observed.

Visual observation of the samples showed no color change, except of the sample stored in open container at daylight (see Table IV.). The moisture absorption of the samples—stored at 76% RH.—was remarkable, without significant discoloration (Table V.)

TABLE IV

Omeprazole content of the samples after two weeks storage under stressed conditions and 6 months storage at ambient temperature

| storage conditions | storage period | omeprazole content (%* + SD) "a" | "b" | Appearance |
|---|---|---|---|---|
| — | — | 12.3 ± 0.08 | 12.0 ± 0.10 | off white powder |
| 40° C., 76% RH ambient temperature | 2 weeks | 12.0 ± 0.06 | 11.7 ± 0.05 | not changed |
| - closed container | 6 months | 12.3 ± 0.23 | 12.1 ± 0.23 | not changed |
| - open container | 6 months | | 11.3 ± 0.5 | very light yellowish color |

*related to the dry substance

TABLE V

Moisture absorption of the samples

| storage conditions | storage period | loss on drying (%) "a" | "b" |
|---|---|---|---|
| — | — | 2.79 | 2.16 |
| 40° C., 76% R.H. ambient temperature | 2 weeks | 9.17 | 8.23 |
| -closed container | 6 months | 2.65 | 2.37 |
| - open container | 6 months | — | 4.35 |

EXAMPLE 4

0.64 g omeprazole and 5.08 g β-cyclodextrin (water content: 12%) are homogenized in a mortar, then a solution of 0.33 g lysine in 1.5 ml of 2.5% NH$_3$ is added and homogenization is continued. Finally the obtained suspension is granulated through a laboratory sieve with 0.4 mm and dried at 45° C. for 24 hours. 5.5 g of granules is obtained. omeprazole content: 10.9%

EXAMPLE 5

Sample a:

1.32 g omeprazole, 0.68 g L-arginine, and 10.56 g β-cyclodextrin (water content: 11.9%) were powdered by co-grinding in a ballmill, then kneaded with 3 ml of water for a few minutes. The resulting paste was dried over P$_2$O$_5$ at room temperature in a vacuum exsiccator overnight, ground roughly to granule-size particles.

To characterize the stability of omeprazole in this formulation also the following samples were prepared with and without amino acid and/or β-cyclodextrin (water content:11.98%):

| | |
|---|---|
| Sample b (without β-cyclodextrin): | 1.32 g omeprazole |
| | 0.66 g L-arginine |
| | 9,3 g lactose |
| Sample c (without arginine): | 1.32 g omeprazole |
| | 10,56 g β-cyclodextrin |
| Sample d (without β-CD; mechanical powder mixt. of example 5) | 1.32 g omeprazole |
| | 0.68 g L-arginine |
| | 9.3 g lactose |

The dried products were powdered and mixed with the acidic reacting cellulose-acetate-phthalate (CAP), the amount of CAP was 5 w/w % related to the total amount of powder mixture.

The samples were stored under 50° C. and 76% rel. humidity for 7 days and their discoloration was evaluated visually.

Results are shown in Table VI.

TABLE VI

| Sample | Discoloration after 7 days at 50° C., 76% rel. hum. |
|---|---|
| a (with β-CD) | off white powder |
| c (without β-CD) | brown |
| d (without arginine) | yellowish brown |
| e (without β-CD; mech. mixt.) | deep brown |

EXAMPLE 6

0.40 g omeprazole and 3.28 g γ-cyclodextrin (water content: 4.9%) are homogenized in a mortar. The resulting powder mixture is kneaded for 10 minutes with 2 ml of the aqueous solution of 0.21 g D,L-arginine.

The obtained paste was dried in a vacuum exsiccator over P$_2$O$_5$ for two days at ambient temperature and pulverized manually. 3.6 g of slightly yellowish powder is obtained.

omeprazole content: 10.5%.

EXAMPLE 7

First three mixtures were prepared:
1) 4.1 g omeprazole and 6 g β-cyclodextrin (water content: 11,9%)
2) 25 g β-cyclodextrin and 55 g water
3) 21 g water and 2,1 g L-arginine Then the three mixtures were mixed together and the resulting suspension was spray-dried under the following conditions:

inlet temperature: 120–125° C.

outlet temperature: 75–80° C.

air pressure: 2.5 kg/cm$^2$ feeding speed: 4 ml/min 37.5 g off-white powder is obtained.

omeprazole content: 12.6%

L-arginine content: 6.22% water content (KFT): 5.40%

EXAMPLE 8

509 g pharmaceutical formulation (omeprazole: β-cyclodextrin: arginine) (1:2:1), 163 g microcrystalline cellulose and 55 g hydroxypropylcellulose are mixed for 5 minutes. Then 270 g isopropanol are given to the mixture and mixed for 10 minutes on high level. After that the mixture is extruded and instantly worked up to pellets. The pellets are dried for about 16–18 hours at 40° C.

The pellets can be filled into hard gelantine capsules optionally enteric coated. Or the pellets are enteric coated with Eudragit L, for example L 100 —55, L100 or L 30D according to standard methods.

What is claimed is:

1. A pharmaceutical formulation comprising
   a benzimidazole compound as active ingredient, and as excipients
   a cyclodextrin selected from the group consisting of β-cyclodextrin and γ-cyclodextrin and
   at least one amino acid
   wherein the benzimidazole compound, the at least one cyclodextrin and the at least one amino acid are contained in a core coated directly with an enteric coating layer.

2. Pharmaceutical formulation according to claim 1, in which the benzimidazole compound decomposes in the presence of humidity.

3. Pharmaceutical formulation according to claim 1, in which the benzimidazole compound is omeprazole.

4. Pharmaceutical formulation according to claim 1, in which the cyclodextrin is β-cyclodextrin.

5. Pharmaceutical formulation according to claim 1, in which the amino acid is a dipeptide or a pharmaceutically acceptable derivated amino acid.

6. Pharmaceutical formulation according to claim 3, wherein the molar ratio of omeprazole to cyclodextrin of from 1 to 10.

7. Pharmaceutical formulation according to claim 3, wherein the molar ratio of amino acid to omeprazole is of from 0.5 to 10.

8. Pharmaceutical formulation according to claim 1 in powdered, granulated or pelletized form.

9. Pharmaceutical formulation according to claim 8, wherein the powder, the granulate or the pelletized formulation is contained in a capsule.

10. Pharmaceutical formulation according to claim 8, wherein the particles of the powder, of the granulate or of the pelletized formulation are contained in a capsule which is not provided with an enteric coating.

11. A process for the production of the pharmaceutical formulation according to claim 1, wherein
   (i) a benzimidazole compound, at least one cyclodextrin and at least one amino acid are wetted with water and mixed;
   (ii) the resulting mixture is dried.

12. A process for the production of a pharmaceutic composition according to claim 1, wherein
   (i) a benzimidazole compound at least one cyclodextrin and at least one amino acid are wetted with water and mixed;
   (ii) the resulting mixture is dried; and
   (iii) discoloration of the composition is examined and if a discolored product is obtained, said discolored product is discarded, another amino acid is selected and steps (i) to (iii) are repeated until an uncolored product is obtained.

13. The process according to claim 11, wherein in step (i) of claim 11 the mixing is carried out by wet-kneading.

14. The process according to any of claims 11, wherein in step (i) of claim 11 the water is ammoniacal water or is free of ammonia.

15. The process according to any of claims 11, wherein in step (ii) of claim 11 the drying is carried out by freeze-drying, spray-drying or vacuum-drying.

16. Pharmaceutical formulation according to claim 2, in which the benzimidazole compound decomposes at a $pH \leq 11$.

17. Pharmaceutical formulation according to claim 16, in which the benzimidazole compound decomposes at a $pH \leq 11$.

18. Pharmaceutical formulation according to claim 5 in which the amino acid is arginine, lysine or hydroxy lysine.

19. Pharmaceutical formulation according to claim 18 in which the amino acid is L-arginine, L-lysine or L-hydroxy lysine.

20. Pharmaceutical formulation according to claim 6, wherein the molar ratio of omeprazole to cyclodextrin is of from 1 to 2.

21. Pharmaceutical formulation according to claim 7, wherein the molar ratio of amino acid to omeprazole is of from 1 to 1.

22. Pharmaceutical formulation according to claim 7, wherein the molar ratio of L-arginine to omeprazole is of from 0.5 to 10.

23. Pharmaceutical formulation according to claim 8, wherein the powdered, granulated or pelletized form has been processed to tablets.

24. Process according to claim 12, wherein in step (i) the mixing is carried out by wet-kneading.

25. Process according to claim 12, wherein in step (i) the water is ammoniacal water or is free of ammonia.

26. Process according to claim 12, wherein in step (ii) the drying is carried out by freeze-drying, spray-drying or vacuum-drying.

27. Pharmaceutical formulation according to claim 8, wherein
   (i) the powder particles, granulate particles or the pellets are provided with the enteric coating or
   (ii) the powder particles, granulate particles or the pellets are not provided with an enteric coating, but processed to tablets as the said core coated directly with the said enteric coating layer to form the pharmaceutical composition.

28. Pharmaceutical formulation according to claim 1, further comprising a binding agent and an excipient.

* * * * *